United States Patent [19]

Rosenberger

[11] 4,216,312

[45] Aug. 5, 1980

[54] FURYL SUBSTITUTED POLYENES

[75] Inventor: Michael Rosenberger, Caldwell, N.J.

[73] Assignee: Hoffmann-La Roche Inc., Nutley, N.J.

[21] Appl. No.: 936,467

[22] Filed: Aug. 24, 1978

[51] Int. Cl.$^2$ ............... C07D 307/40; C07D 307/46; C07D 407/12

[52] U.S. Cl. ............... 542/427; 260/347.3; 260/347.4; 260/347.5; 260/347.8; 424/250; 424/285

[58] Field of Search ............... 260/347.3, 347.4, 347.5, 260/347.8; 542/427

[56] References Cited

U.S. PATENT DOCUMENTS

| | | | |
|---|---|---|---|
| 3,984,440 | 10/1976 | Bollag et al. | 260/345.2 |
| 4,061,656 | 12/1977 | Klaus et al. | 542/427 X |
| 4,086,420 | 4/1978 | Tsuchihashi et al. | 542/427 X |
| 4,147,708 | 4/1979 | Manchand | 260/413 |

FOREIGN PATENT DOCUMENTS 866651 3/1978 Belgium.
861982 6/1978 Belgium.

OTHER PUBLICATIONS

Englert, Helv. Chimica Acta, 58(1975), pp. 2367, 2375, 2376.
Wilkoff et al., Chem. Abstracts, 84(1976), #173605.

*Primary Examiner*—Arthur P. Demers
*Attorney, Agent, or Firm*—Jon S. Saxe; Bernard S. Leon; George W. Johnston

[57] ABSTRACT

9-Furyl substituted retinoic acid derivatives which are useful as antitumor agents and in the treatment of acne as well as a method for their manufacture are disclosed.

24 Claims, No Drawings

FURYL SUBSTITUTED POLYENES

SUMMARY

The present invention concerns compounds of the formula:

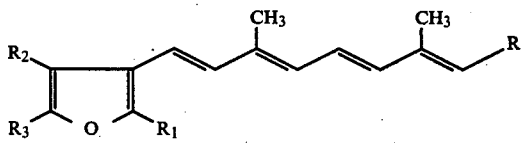

wherein $R_1$ and $R_2$ each are lower alkyl; $R_3$ is hydrogen or lower alkyl; and R is

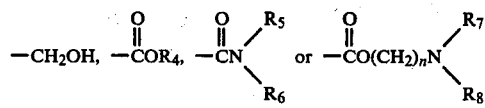

wherein $R_4$ is hydrogen or lower alkyl; $R_5$, $R_6$, $R_7$ and $R_8$ individually are hydrogen or lower alkyl; $R_7$ and $R_8$ can be taken together with the attached nitrogen atom to form a 5 or 6 membered heterocyclic ring which can contain one additional hetero atom selected from the group consisting of nitrogen, oxygen and sulfur, and which hetero atom can be unsubstituted or substituted with lower alkyl; and n is 2 or 3; with the proviso that when $R_7$ and $R_8$ are taken together to form a 5 or 6 membered heterocyclic ring which contains an additional nitrogen atom, said additional nitrogen atom is lower alkyl substituted;

or the pharmaceutically acceptable salts thereof.

The compounds of formula I are useful as antitumor agents and for treating acne, psoriasis and other related dermatological disorders.

The compounds of formula I are manufactured in accordance with the reaction sequence noted in Schemes 1, 2 and 3, described hereinafter.

DETAILED DESCRIPTION OF THE INVENTION

The present invention concerns polyene compounds, a process for their manufacture and pharmaceutical preparations containing same.

The polyene compounds included within the present invention have the formula:

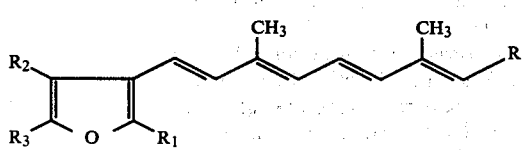

wherein $R_1$ and $R_2$ each are lower alkyl; $R_3$ is hydrogen or lower alkyl; and R is

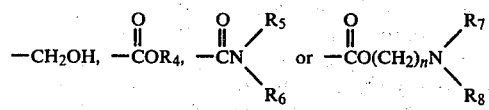

wherein $R_4$ is hydrogen or lower alkyl; $R_5$, $R_6$, $R_7$ and $R_8$ individually are hydrogen or lower alkyl; $R_7$ and $R_8$ can be taken together with the attached nitrogen atom to form a 5 or 6 membered heterocyclic ring which can contain one additional hetero atom selected from the group consisting of nitrogen, oxygen and sulfur, and which hetero atom can be unsubstituted or substituted with lower alkyl; and n is 2 or 3; with the proviso that when $R_7$ and $R_8$ are taken together to form a 5 or 6 membered heterocyclic ring which contains an additional nitrogen atom, said additional nitrogen atom is lower alkyl substituted;

or the pharmaceutically acceptable salts thereof.

As used herein, lower alkyl means an alkyl group having from 1 to 7 carbon atoms, (e.g., methyl, ethyl, n-propyl and isopropyl). Lower alkoxy means an alkoxy group having from 1 to 7 carbon atoms (e.g., methoxy, ethoxy and isopropoxy). Alkoxymethyl and alkoxycarbonyl include straight chain or branched-chain alkoxy groups having from 1 to 20 carbon atoms (e.g., methoxy, ethoxy, isopropoxy and cetyloxy). A lower alkoxy group contains from 1 to 7 carbon atoms. Aryl denotes mononuclear aromatic hydrocarbon groups such as phenyl, benzyl and the like which can be unsubstituted or substituted in one or more positions with halogen, nitrogen, lower alkyl or lower alkoxy and polynuclear aromatic hydrocarbon groups such as napthyl, anthryl, phenanthryl, azulyl and the like which can be unsubstituted or substituted with one or more of the aforementioned substituents. A atom means an atom other than carbon in an atomic ring and selected from the group consisting of nitrogen, oxygen and sulfur.

An alkanoyloxy group of an alkanoyloxymethyl group is derived from an alkanecarboxylic acid having from 1 to 20 carbon atoms (e.g., acetic acid, propionic acid, pivalic acid, palmitic acid and stearic acid). The preferred group of alkanecarboxylic acids are lower alkanecarboxylic acids having from 1 to 7 carbon atoms. The carbamoyl groups within the scope of this invention can be monosubstituted or disubstituted by straight chain or branched chain lower alkyl groups. Examples of such substituted carbamoyl groups are methyl carbamoyl, dimethylcarbamoyl, diethylcarbamoyl and methyl ethyl carbamoyl. Halogen includes all four halogens which are fluorine, chlorine, bromine and iodine. Alkali metals include lithium, sodium, potassium and rubidium. Alkaline earth metals include beryllium, magnesium, calcium and strontium. Pharmaceutically acceptable salts means any conventional pharmaceutically acceptable salt. Among the preferred salts are alkali metal, alkaline earth metal (e.g., sodium, potassium and calcium) and substituted or unsubstituted ammonium salts.

Unless otherwise indicated, all formulas include cis/trans mixtures as well as the corresponding cis and trans compounds.

All trans compounds of formula I are preferred. Additionally, compounds of formula I wherein R is

$-COR_4$, and $R_4$ is hydrogen or lower alkyl as well as the alkali metal pharmaceutically acceptable salts thereof are also preferred. Furthermore, compounds of formula I wherein R is

SCHEME 1

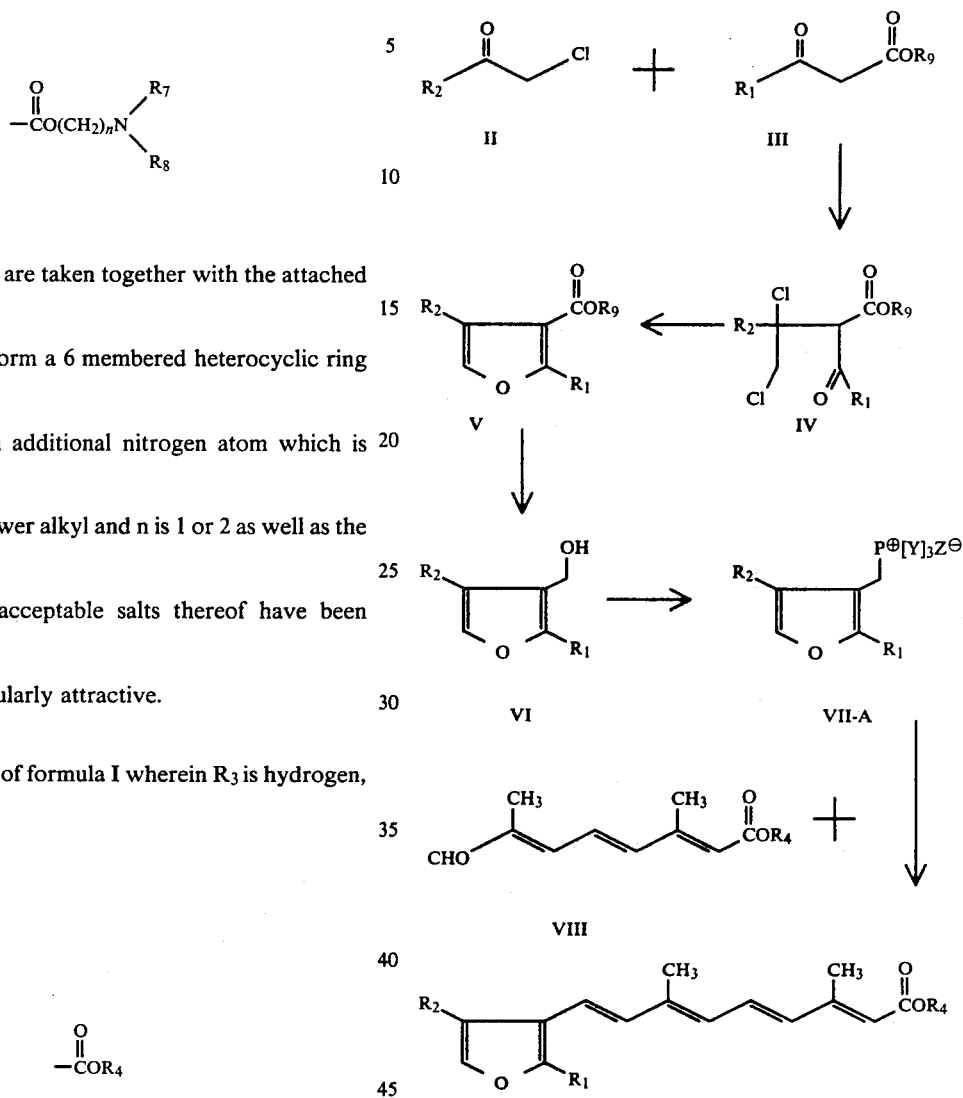

wherein $R_7$ and $R_8$ are taken together with the attached nitrogen atom to form a 6 membered heterocyclic ring which contains an additional nitrogen atom which is substituted with lower alkyl and n is 1 or 2 as well as the pharmaceutically acceptable salts thereof have been found to be particularly attractive.

The compounds of formula I wherein $R_3$ is hydrogen, R is $$-\overset{O}{\underset{\|}{C}}OR_4$$

and $R_4$ is lower alkyl can be prepared from a compound of the formula:

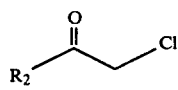

II wherein $R_2$ is lower alkyl in accordance with the following scheme:

wherein $R_1$, $R_2$, $R_4$ and $R_9$ each are lower alkyl, Y is aryl and Z is the anion of an inorganic or organic acid.

In accordance with Scheme 1, chloro-ketone of formula II is reacted with a betaketo-ester of formula III via an alkylation reaction to form compound IV wherein $R_1$, $R_2$ and $R_9$ are as above. A suitable method includes reacting compounds II and III with hydrochloric or hydrobromic acid. Although temperature is not critical, the reaction generally occurs between about $-10°$ and about $23°$ C., preferably at about $0°$ C.

Compound IV then is converted via internal alkylation to compound V wherein $R_1$, $R_2$ and $R_9$ are as above. Any inorganic (e.g., alkali metal or alkaline earth metal hydroxide or carbonate) or organic (e.g., tertiary amines such as triethylamine and pyridine) base may be utilized in this conversion. The reaction proceeds in any inert organic solvent or in the presence of excess organic base. Although temperature is not critical, the temperature for the conversion of compound IV to compound V generally ranges from about 0° to about 100° C. Room temperature is preferred.

Compound V is reduced to compound VI wherein $R_1$ and $R_2$ are as above by any conventional method for reducing an ester to an alcohol. An applicable method includes treating compound V with diisobutyl aluminum hydride or lithium aluminum hydride. With this method, temperature is not critical and can range from about $-20°$ to about 30° C. Preferably the temperature is maintained at about 0° C.

Compound VI is converted via a Wittig reaction to compound VII-A wherein $R_1$ and $R_2$ each are lower alkyl, Y is aryl and Z is the anion of an organic or inorganic acid. The conversion of compound VI to compound VII-A is carried under conventional Wittig procedures and conditions. For example, compound VI can be reacted in the presence of a triarylphosphine hydrohalide or triarylphosphine hydrosulfate such as triphenylphosphine hydrobromide and triphenylphosphine hydrosulfate. Although temperature is not critical, the reaction generally proceeds between about $-10°$ and about 40° C. Room temperature is preferred.

In formula VII-A, aryl denoted by Y includes all aryl groups and preferably mononuclear substituted and unsubstituted aryl groups such as phenyl, lower alkyl phenyl and lower alkoxy phenyl (e.g., tolyl, zylyl, mesityl and p-methoxyphenyl). The inorganic acid and ions denoted by Z include, for example, chloride, bromide, iodide and hydrosulfate ions. A preferred organic acid anion for Z is the tosyloxy ion.

Compound VII-A is reacted with compound VIII via a Wittig reaction to form compounds of formula I wherein $R_1$ and $R_2$ each are lower alkyl, $R_3$ is hydrogen, R is $$-\overset{O}{\underset{||}{C}}OR_4$$

and $R_4$ is lower alkyl. The resulting compounds have the formula:

I-A wherein $R_1$, $R_2$ and $R_4$ each are lower alkyl.

The Wittig reaction of compound VII-A and VIII occurs under conventional Wittig procedures and conditions. Compounds VII-A and VIII are reacted in the presence of an inorganic or organic acid binding agent. Typical acid binding agents include alkyllithium (e.g., n-butyllithium and methyllithium), aryllithium (e.g., phenyllithium), alkali metal hydroxides and alcoholates (e.g., sodium hydroxide and potassium alcoholate). Although not necessary, the reaction can proceed in an inert solvent such as diethyl ether and tetrahydrofuran or an aliphatic or aromatic hydrocarbon such as hexane, benzene or toluene. The temperature of the reaction is not critical but the reaction generally occurs between about 0° C. and about 35° C. Preferably the reaction proceeds at room temperature.

The compounds of formula VIII are known or can be prepared from known compounds by conventional procedures.

In accordance with another aspect of the present invention, compounds of formula I wherein $R_3$ is lower alkyl, R is $$-\overset{O}{\underset{||}{C}}OR_4$$

and $R_4$ is lower alkyl can be formed by the following reaction scheme:

SCHEME 2 wherein $R_1$, $R_2$, $R_3$, $R_4$ and $R_9$ each are lower alkyl, Y is aryl and Z is the anion of an inorganic or organic acid.

In accordance with Scheme 2, haloketo of formula IX is reacted with beta-keto ester of formula III via alkylation to form compound X wherein $R_1$–$R_3$ and $R_9$ each are lower alkyl. Typical alkylating means include reacting compound IX and compound III in the presence of an alkali metal or alkaline earth metal alkoxide (e.g., potassium methoxide and sodium ethoxide). The reaction proceeds in the presence of a solvent such as an organic alcohol (e.g., methanol, ethanol and isopropanol). Although the temperature is not critical, the reaction generally proceeds between about room temperature and the reflux temperature of the reaction mixture. Room temperature is preferred.

Compound X is converted via cyclization to compound XI wherein $R_1$–$R_3$ and $R_9$ each are lower alkyl. The reaction can occur in the presence of any strong organic (e.g., paratoluenesulfonic acid and trifluoroacetic acid) or inorganic (e.g., hydrochloric acid, sulfuric acid and perchloric acid) acid. The reaction preferably occurs under aqueous conditions. Although not critical, the reaction temperature range is generally about room temperature to about 110° C. Preferably, the reaction proceeds at about 100° C.

Compound XI is converted to compound XII wherein $R_1$–$R_3$ each are as above by any conventional method for reducing an ester to an alcohol. A suitable method includes reacting compound XI in the presence of diisobutylaluminum hydride or lithium aluminum hydride. The temperature of the reaction is not critical but the reaction generally occurs between about −20° to about 30° C. A temperature of 0° C. is preferred.

Compound XII can then be converted via a Wittig reaction to compound VII-B wherein $R_1$, $R_2$ and $R_3$ each are lower alkyl, Y is aryl and Z is an anion of an inorganic or organic acid.

The reaction of compound XII to compound VII-B proceeds under the conventional Wittig procedures and conditions. According to the Wittig reaction, compound XII is reacted in the presence of an acid binding agent such as triarylphsophine hydrohalide or triarylphosphine hydrosulfate as described above in the conversion of compound VI to compound VII-A.

In formula VII-B, aryl denoted by Y includes all aryl groups and preferably substituted and unsubstituted mononuclear aryl groups such as phenyl, lower alkyl phenyl and lower alkoxy phenyl (e.g., tolyl, zylyl, mesityl and p-methoxyphenyl). The inorganic acid and ions denoted by Z includes, for example, chloride, bromide, iodide and hydrosulfate ions. A preferred organic acid anion for Z is the tosyloxy ion.

Compound VII-B then can be reacted via a Wittig reaction with compound VIII to form compounds of formula I wherein $R_3$ is lower alkyl, R is $$-COR_4$$

and $R_4$ is lower alkyl.

The resulting compounds have the formula:

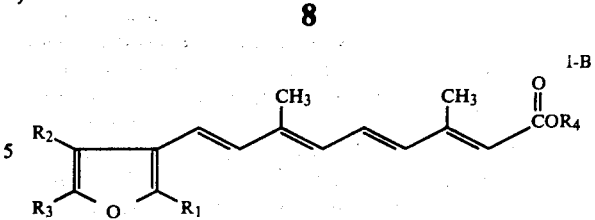

wherein $R_1$–$R_4$ each are lower alkyl.

According to the Wittig procedure, compound VII-B is reacted with compound VIII in the presence of an inorganic or organic acid binding agent. Typical acid binding agents and the conventional Wittig procedures have been previously described with respect to the reaction of compound VII-A with compound VIII.

The compounds of formula I-A and I-B are collectively referred to as compounds of the formula:

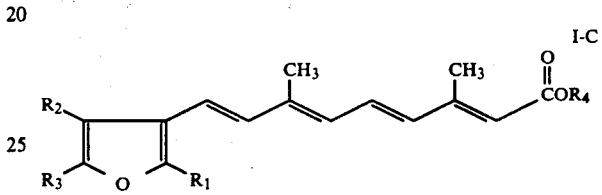

wherein $R_1$, $R_2$ and $R_4$ are lower alkyl and $R_3$ is hydrogen or lower alkyl.

According to the present invention, conventional procedures may be applied to compound I-C to produce compounds of formula I wherein R is

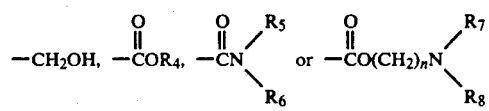

wherein $R_4$ is hydrogen; $R_5$, $R_6$, $R_7$ and $R_8$ individually are hydrogen or lower alkyl; $R_7$ and $R_8$ can be taken together with the attached nitrogen atom to form a 5 or 6 membered heterocyclic ring which can contain one additional hetero atom selected from the group consisting of nitrogen, oxygen and sulfur, and hetero atom which can be unsubstituted or substituted with lower alkyl; and n is 2 or 3; with the proviso that when $R_7$ and $R_8$ are taken together to form a 5 or 6 membered heterocyclic ring which contains an additional nitrogen atom, said additional nitrogen atom is lower alkyl substituted.

Typical processes contemplated by the present invention include: reducing a carboxylic acid ester of formula I which was obtained according to the above procedures to its corresponding alcohol; hydrolyzing a carboxylic acid ester of formula I to its corresponding carboxylic acid, amidating the resulting carboxylic acid to its corresponding amide; and converting the carboxylic acid of formula I to its corresponding alkyl amino ester via an alkyl amino alcohol.

More particularly, the reaction sequence for converting compound I-C to various compounds within formula I is set in the following reaction Scheme:

SCHEME 3

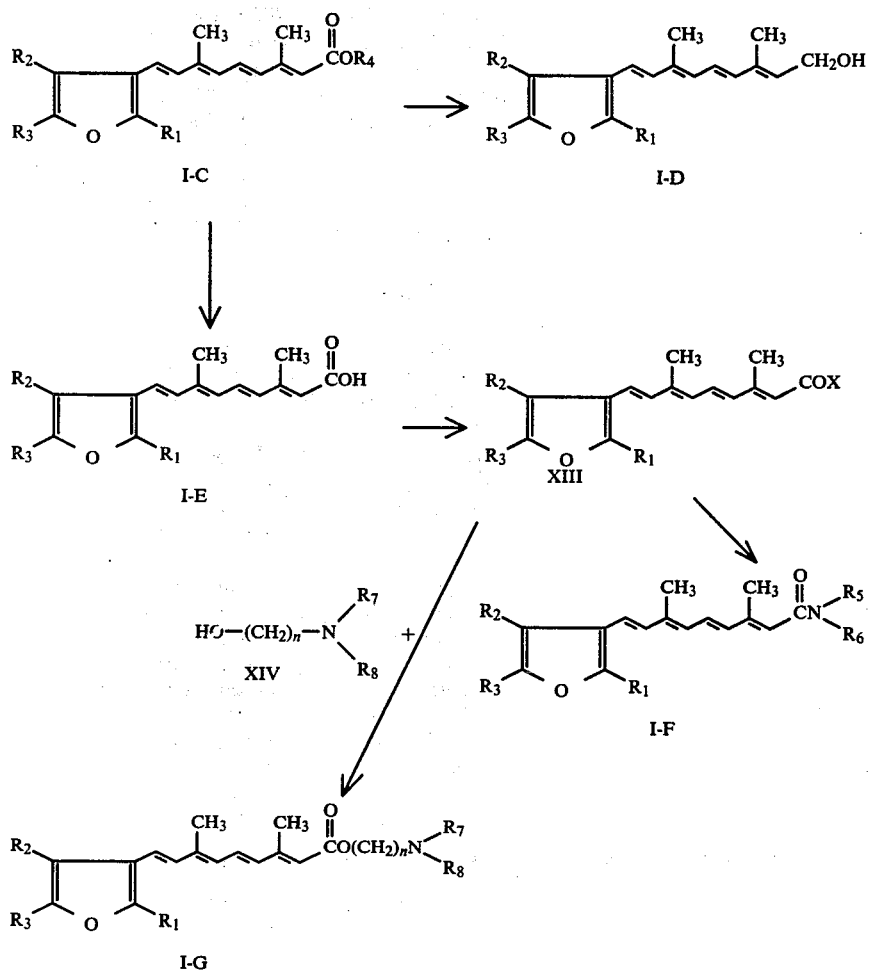

wherein $R_1$ and $R_2$ each are lower alkyl: $R_3$ is hydrogen or lower alkyl; $R_4$ is hydrogen or lower alkyl; $R_5$, $R_6$, $R_7$ and $R_8$ individually are hydrogen or lower alkyl; $R_7$ and $R_8$ can be taken together with the attached nitrogen atom to form a 5 or 6 membered heterocyclic ring which can contain one additional hetero atom selected from the group consisting of nitrogen, oxygen and sulfur, and which hetero atom can be unsubstituted or substituted with lower alkyl; n is 2 or 3; and X is halogen; with the proviso that when $R_7$ and $R_8$ are taken together to form a 5 or 6 membered heterocyclic ring which contains an additional nitrogen atom, said additional nitrogen atom is lower alkyl substituted.

Compound I-C can be converted to alcohol I-D wherein $R_1$–$R_3$ are as above by reduction. Any conventional method for reducing an ester to an alcohol can be utilized to carry out this conversion. A preferred reduction method is to react compound I-C with diisobutylaluminum hydride in diether solvent to produce alcohol I-D. Although temperature is not critical, the reaction proceeds between a temperature of about −50° C. to about 40° C. A temperature of 0° C. is preferred.

Compound I-C can also be converted to acids of formula I-E wherein $R_1$–$R_3$ are as above by basic hydrolysis. Any conventional method for hydrolyzing an ester to an acid may be employed. A typical method includes reacting compound I-C in an alkali metal or alkaline earth metal hydroxide (e.g., potassium hydroxide) and in an aqueous alcohol (e.g., methanol and propanol). Temperature is not critical but can vary from about 50° to about 100° C. A temperature of about 80° C. is preferred.

Compound I-E then can be converted to amides of formula I-F via an acid halide intermediate of the formula:

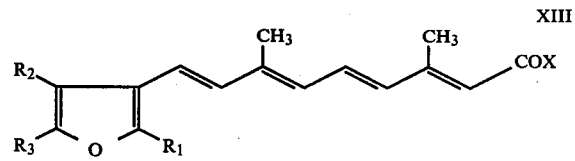

wherein $R_1$ and $R_2$ are lower alkyl, $R_3$ is hydrogen or lower alkyl and X is halogen.

More particularly, compound I-E is converted to its corresponding acid halide of formula XIII by any conventional method for forming an acid halide form a carboxylic acid. A preferred technique includes utilizing oxalyl chloride as a halogenating agent in benzene in the presence of catalytic amounts of dimethylformamide. Although temperature is not critical, the general range of temperature is from about −10° C. to about 30° C. The preferred temperature is about 5° C.

Acid halide XIII then can be converted to an unsubstituted amide or lower alkyl substituted amide of formula I-F wherein $R_1$-$R_3$ and $R_5$-$R_6$ are as above. Any conventional method for forming an unsubstituted amide or lower alkyl substituted amide (i.e., mono(-lower alkyl)-carbamoyl or di(lower alkyl)-carbamoyl) from its corresponding acid chloride can be utilized. For example, acid halide XIII can be reacted with ammonia or an amine preferably in a solvent such as diethyl ether to produce compounds of formula I-F. Although the temperature is not critical, the temperature can range from about $-20°$ to about $30°$ C. The preferred temperature is $0°$ C.

Additionally, the carboxylic acids I-E can be converted to the compounds of formula I-G via acid halide intermediate XIII and alkyl amino alcohol intermediate XIV of the formula:

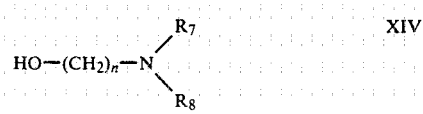

wherein $R_1$ and $R_2$ each are lower alkyl; $R_3$ is hydrogen or lower alkyl; $R_7$ and $R_8$ individually are hydrogen or lower alkyl or $R_7$ and $R_8$ can be taken together with the attached nitrogen atom to form a 5 or 6 membered heterocyclic ring which can contain one additional hetero atom selected from the group consisting of nitrogen, oxygen and sulfur, and which hetero atom can be unsubstituted or substituted with lower alkyl; and n is 2 or 3; with the proviso that when $R_7$ and $R_8$ are taken together to form a 5 or 6 membered heterocyclic ring which contains an additional nitrogen atom, said additional nitrogen atom is lower alkyl substituted.

The compounds of formula XIV are known or can be prepared from known compounds.

Compound I-E can be converted to its corresponding acid halide XIII as described above.

Compound XIII then can be reacted with compound XIV via esterification to form compounds I-G wherein $R_1$-$R_3$, $R_7$, $R_8$ and n are as above. Any conventional method of reacting an acid halide with an alkyl amino alcohol to form an ester may be employed. For example, an acid chloride of formula XIII can be reacted with an alkyl amino alcohol of formula XIV (e.g., N-methyl-N-hydroxyethyl piperazine, N-ethyl-N-hydroxyethyl piperazine, N-hydroxyethyl morpholine, N-hydroxyethyl piperazine, N-methyl-N-hydroxypropyl piperazine, N-hydroxypropyl morpholine and N-hydroxypropyl piperazine) in triethylamine to produce compound I-G. Although temperature is not critical, the temperature can vary from about $0°$ C. to about $50°$ C. Room temperature is preferred.

Preferred alkyl amino esters and their pharmaceutically acceptable salts are compounds of formula I-G wherein $R_7$ and $R_8$ can be taken together with the attached nitrogen to form a 6 membered heterocyclic ring which contains a lower alkyl substituted additional nitrogen atom that is positioned para to the other nitrogen atom. Such alkyl amino esters are preferred because their salts formed with mineral acids are water soluble. These alkyl amino esters have the formula:

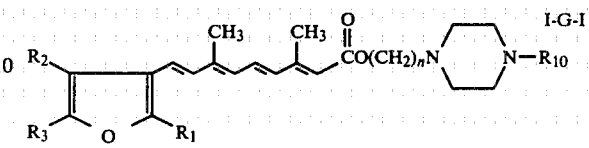

wherein $R_1$, $R_2$ and $R_{10}$ each are lower alkyl, $R_3$ is hydrogen or lower alkyl and n is 2 or 3.

(E,E,E,E)-3,7-dimethyl-9-[(2,4,5-trimethyl)-3-furyl]-2,4,6,8-nonatetraenoic acid 4-methyl-1-(2-ethylpiperazinyl)ester and (E,E,E,E)-3,7-dimethyl-9-[(2,4-trimethyl)-3-furyl]-2,4,6,8-nonatetraenoic acid 4-methyl-1-(2-ethylpiperazinyl) ester and their bishydrochloride salts are particularly preferred compounds within formula I-G-1.

The compounds of formula I can occur as a cis-trans mixture which can be separated in a known manner into the corresponding cis and trans components or isomerized in a known manner to the all-trans compounds. Any conventional method of double bond isomerization can be utilized to form the all-trans compound. For example, a cis/trans mixture of compound I can be treated with catalytic amounts of iodine in an organic solvent (e.g., benzene and toluene) to produce the desired all-trans product. Although temperature is not critical, the isomerization generally occurs between about $10°$ to about $60°$ C. The preferred temperature values are from about $25°$ to about $35°$ C.

The compounds of formula I are pharmacodynamically valuable. They are effective in regressing the growth of tumors such as papillomas as well as in regressing the growth of chondrosarcoma.

The compounds of formula I are also useful as medicaments for the topical and systemic therapy of acne, psoriasis and other related dermatological disorders which are characterized by an increased or pathologically altered cornification, as well as inflammatory and allergic dermatological conditions. They can also be used to treated disorders which are characterized by inflammatory or degenerative alterations of the mucous membranes. Advantageously, the invention compounds are only slightly toxic.

To examine their pharmacodynamic properties, the compounds of the present invention were subjected to skin papilloma tests as described by W. Bollag in *Experentia*, Vol. 27 (1971) pp. 90 et seq. and to hypervitaminosis-A dosage experiments as defined by W. Bollag in *Europ. J. Cancer*, Vol. 10 (1974) pp. 731-737. The following Table illustrates the results obtained from the inventive compounds utilizing these tests.

TABLE 1

| Compound | Hypervitaminosis dose mg/kg/day | Papilloma Effect Dose mg/kg/day | Papilloma Effect Effect ± % regression |
|---|---|---|---|
| (E,E,E,E)-3,7-dimethyl-9-(2,4-dimethyl-3-furyl)-2,4,6,8-nonatetraenoic acid ethyl ester | >400 | 80 | −29 |
| (E,E,E,E)-3,7-dimethyl-9-(2,4,5-trimethyl-3-furyl)-2,4,6,8-nonatetraenoic acid ethyl ester | 200 | 40 | −63 |
| Potassium (E,E,E,E)-3,7-dimethyl-9-(2,4,5-trimethyl-3-furyl)-2,4,6,8-nonatetraenoate | 50 | 20 | −17 |

TABLE 1-continued

| Compound | Hypervitaminosis dose mg/kg/day | Papilloma Effect Dose mg/kg/day | Papilloma Effect Effect ± % regression |
|---|---|---|---|
| Potassium (E,E,E,E)-3,7-dimethyl-9-(2,4-dimethyl-3-furyl)-2,4,6,8-nonatetraenoate | 200 | 80 | −14 |
| (E,E,E,E)-3,7-dimethyl-9-(2,4-dimethyl-3-furyl)-2,4,6,8-nonatetraenoic acid | 100 | 40 | −44 |

The compounds of formula I can be used as medicaments in the form of pharmaceutical preparations. At least one of the compounds of formula I can be utilized in association with a compatible carrier material to form the pharmaceutical preparations.

Illustratively, pharmaceutical preparations for systemic administration can be prepared by adding a polyene compound of formula I as the active ingredient to pharmaceutically acceptable, non-toxic, inert, solid or liquid carriers which are usually included in such preparations. The pharmaceutical preparations can be administered enterally, parenterally or topically. Suitable preparations for enteral administration are, for example, tablets, capsules, dragees, syrups, suspensions, solutions and suppositories. Suitable pharmaceutical preparations for parenteral administration are infusion solutions.

The dosages in which the compounds are administered can be varied according to the mode and route of administration and according to the requirements of the patient. For example, the compounds can be administered in amounts of from 0.5 mg. to 100 mg. daily in one or more dosages.

In addition to the active compounds of this invention, the pharmaceutical preparations can contain pharmaceutically acceptable inert or pharmacodynamically active additives. For example, tablets or granules can contain a series of pharmaceutically acceptable binders, fillers, carrier materials or diluents. Liquid preparations can, for example, take the form of sterile water-miscible solutions. Capsules can contain a pharmaceutically acceptable filler or thickener. Furthermore, pharmaceutically acceptable flavor improving additives and pharmaceutically acceptable substances commonly used as preservatives, stabilizers, moisture retainers or emulsifiers, salts for varying the osmotic pressure, buffers and other pharmaceutically acceptable additives can also be present in the pharmaceutical preparations.

The aforementioned pharmaceutically acceptable carrier materials and diluents are well known to the pharmaceutical compounding art and can be organic or inorganic substances such as water, gelatin, lactose, magnesium, stearate, talc, gum arabic, polyalkyleneglycols and the like. It is, of course, a prerequisite that all adjuvants used in the preparation of the pharmaceutical preparations are non-toxic and pharmaceutically acceptable.

For topical administration, the compounds of this invention are expediently prepared as salves, tinctures, creams, solutions, lotions, sprays, suspensions and the like. Ointments, creams and solutions are preferred. These pharmaceutical preparations for topical administration can be prepared by mixing a compound of this invention as the active ingredient with pharmaceutically acceptable non-toxic, inert, solid or liquid carriers which are customary in such preparations and which are suitable for topical administration.

Conventional pharmaceutically acceptable antioxidants (e.g., tocopherol, N-methyl-alpha-tocopheramine butylated hydroxyanisole and butylated hydroxytoluene) can also be incorporated into the pharmaceutical preparations containing the polyene compounds of this invention.

The following Examples illustrate the present invention. Unless otherwise stated the ether is diethyl ether and temperatures are expressed in degrees Celsius.

EXAMPLE 1

(2,4-dimethyl-3-furyl)methyl triphenylphosphonium bromide 2,4-Dimethyl-3-carbethoxyfuran (42.8 g.) prepared in accordance with J. Amer. Chem. Soc., v. 73, 356 (1951) was dissolved in ether (100 ml.) and added slowly to a cooled (0°) slurry of lithium aluminum hydride (10 g.) in ether (200 ml.) and the mixture was then stirred at room temperature for 18 hours. After this time, the mixture was cooled in an ice bath and quenched with an aqueous solution of sodium sulfate (60 ml.; saturated) followed by the addition of solid magnesium sulfate. The solids were filtered off, washed well with additional ether and the combined ether extract was concentrated to yield 2,4-dimethyl-3-hydroxymethylfuran. Distillation gave pure 2,4-dimethyl-3-hydroxymethylfuran (21.1 g.) bp 63°–65° at 2 mm Hg.

A solution of 2,4-dimethyl-3-hydroxymethylfuran (11 g.) in dichlormethane (25 ml.) was added to a cooled slurry of triphenylphosphine hydrobromide (34 g.) in dichloromethane to give a clear solution. After standing a further 30 minutes at room temperature the bulk of the solvent was distilled off and the residue was crystallized from a 1:4 parts by volume mixture of methanol and ethylacetate to yield a buff colored solid (27.2 g.) of (2,4-dimethyl-3-furyl)methyl triphenylphosphonium bromide, m.p. 248°–249°.

EXAMPLE 2

(E,E,E,E)-3,7-dimethyl-9-(2,4-dimethyl-3-furyl)-2,4,6,8-nonatetraenoic acid ethyl ester A suspension of (2,4-dimethyl-3-furyl) methyl triphenylphosphonium bromide (21.3 g.) in tetrahydrofuran (200 ml.) was cooled to −20° and treated with a solution of n-butyllithium in hexane (33.5 ml.; 1.6 M) and then stirred for a further 15 minutes at −20°. To this solution was added (E,E,E)-3-methyl-7-formyl-2,4,6-octatrienoic acid, ethyl ester (9.1 g.) dissolved in tetrahydrofuran (50 ml.) and the reaction mixture was then stirred a further 30 minutes at −20°.

Ether was then added and the mixture was washed with a saturated brine solution and then concentrated to yield a mixture (28.2 g.) of triphenylphosphine oxide and (E,E,E,E)-3,7-dimethyl-9-(2,4-dimethyl-3-furyl)-2,4,6,8-nonatetraenoic acid ethyl ester. This crude material was extracted several times with hexane (5×100 ml.) and the hexane extracts were then taken to dryness. The residue (16.4 g.) was dissolved in a hexane-ethylacetate mixture (4:1 parts by volume) and filtered through a silica gel column (200 g.). Elution with the same solvent system (700 ml.) yielded the retinoid fraction (13.5 g.). Crystallization from hexane gave pure (E,E,E)-3,7-dimethyl-9-(2,4-dimethyl-3-furyl)-2,4,6,8-nonatetraenoic acid ethyl ester (7.93 g.) m.p. 98°–101°.

EXAMPLE 3

(2,4,5-trimethyl-3-furyl)methyl triphenylphosphonium bromide 2,4,5-Trimethyl-3-carbethoxyfuran (40 g.) prepared in accordance with Helv. Chim. Acta., v. 15, 1112 (1932), was dissolved in ether (200 ml.) and added to a cooled slurry of lithium aluminum hydride (10 g.) in ether (200 ml.) After stirring a further 16 hours at room temperature a saturated, aqueous solution of sodium sulfate was added followed by the addition of magnesium sulfate (50 g.). The solids were filtered off and the solvents were concentrated to give crude alcohol, 2,4,5-trimethyl-3-hydroxymethyl furan (31 g.). A solution of this alcohol (4.2 g.) in dichloromethan (10 ml.) was added to a cooled slurry of triphenylphosphine hydrobromide (10 g.) in dichloromethane (40 ml.) and then left at room temperature for 15 minutes. Ether was then added and the solids formed were crystallized from a 1:5 parts by volume mixture of methanol and ethylacetate to give pure (2,4,5-trimethyl-3-furyl) methyl triphenylphosphonium bromide (10.2 g.) m.p. 223°–224°.

EXAMPLE 4

(E,E,E)-3,7-dimethyl-9-(2,4,5-trimethyl-3-furyl)-2,4,6,8-nonatetraenoic acid ethyl ester A slurry of (2,4,5-trimethyl-3-furyl) methyl triphenylphosphonium bromide (8.2 g.) in tetrahydrofuran (50 ml.) was cooled to −20° and treated with a hexane solution of n-butyllithium (11 ml.; 1.6 M) and stirred a further 15 minutes at −20°. A solution of (E,E,E)-3-methyl-7-formyl-2,4,6-octatrienoic acid ethyl ester (3.1 g.) in tetrahydrofuran (10 ml.) was then added and the resulting mixture was stirred for a further 10 minutes at −10°.

Hexane (400 ml.) was then added and the solids were filtered off. The solvents were taken to dryness to yield a crude retinoid (5.8 g.). Chromatography of this material on silica gel (500 g.) using a 2:3 parts by volume mixture of ethylacetate and hexane followed by crystallization from hexane (twice) yielded (E,E,E)-3,7-dimethyl-9-(2,4,5-trimethyl-3-furyl)-2,4,6,8-nonatetraenoic acid ethyl ester (2.2 g.) m.p. 89°–91°.

EXAMPLE 5

(E,E,E)-3,7-dimethyl-9-(2,4,5-trimethyl-3-furyl)-2,4,6,8-nonatetraenoic acid (E,E,E)-3,7-Dimethyl-9-(2,4,5-trimethyl-3-furyl)-2,4,6,8-nonatetraenoic acid ethyl ester (2.8 g.) was dissolved in ethanol (50 ml.) treated with potassium hydroxide (1.6 g.) in water (5 ml.) and heated at reflux for 30 minutes. After cooling to room temperature, water followed by acetic acid (until acid) was added and the solids were filtered off. Crystallization from ethylacetate gave pure (E,E,E)-3,7-dimethyl-9-(2,4,5-trimethyl-3-furyl)-2,4,6,8-nonatetraenoic acid (1.5 g.) m.p. 213°–214°.

EXAMPLE 6

(E,E,E)-3,7-dimethyl-9-(2,4-dimethyl-3-furyl)-2,4,6,8-nonatetraenoic acid

In accordance to a procedure similar to that of Example 5 (E,E,E)-3,7-dimethyl-9-(2,4-dimethyl-3-furyl)-2,4,6,8-nonatetraenoic acid m.p. 201–203 was prepared from (E,E,E)-3,7-dimethyl-9-(2,4-dimethyl-3-furyl)-2,4,6,8-nonatetraenoic acid ethyl ester by a crystallization from a methanol-ethylacetate mixture.

EXAMPLE 7

(E,E,E)-3,7-dimethyl-9- [(2,4,5-trimethyl)-3-furyl ] -2,4,6,8-nonatetraenoic acid 4-methyl-1-(2-ethylpiperazinyl) ester and (E,E,E)-3,7-dimethyl-9-[(2,4,5-trimethyl)-3-furyl]-2,4,6,8-nonatetraenoic acid 4-methyl-1-(2-ethylpiperazinyl) ester dihydrochloride (E,E,E)-3,7-dimethyl-9-(2,4,5-dimethyl-3-furyl)-2,4,6,8-nonatetraenoic acid (1.5 g.) was mixed with a solution of oxalyl chloride (1 ml.) in benzene (10 ml.) and stirred at room temperature until all the solids had dissolved (about 2 hours; 0.2 ml. dimethylformamide speeds up the reaction).

The solvents were then removed "in vacuo" to yield crude (E,E,E)-3,7-dimethyl-9-(2,4,5-dimethyl-3-furyl)-2,4,6,8-nonatetraenoic acid chloride which was dissolved in ether (25 ml.) and treated with a mixture of N-methyl-N-hydroxyethyl piperazine (1.5 g.), triethylamine (3 ml.) and ether (5 ml.) and left at room temperature for 1 hour. Water and an aqueous sodium carbonate solution was added and the organic materials were extracted into ether. Removal of the solvents gave a crude amino ester as a solid. Crystallization from isopropylether gave pure (E,E,E)-3,7-dimethyl-9-[(2,4,5-trimethyl)-3-furyl]-2,4,6,8-nonatetraenoic acid 4-methyl-1-(2-ethylpiperazinyl) ester (0.6 g.) m.p. 100°–105°.

To make its bishydrochloride salt, the above amino ester was dissolved in ether and added to a cold solution of hydrogen chloride in ether. The yellow water soluble precipitate was filtered off, washed with more ether and dried to yield (E,E,E)-3,7-dimethyl-9-[(2,4,5-trimethyl)-3-furyl]-2,4,6,8-nonatetraenoic acid 4-methyl-1-(2-ethylpiperazinyl) ester dihydrochloride m.p. 200° with decomposition.

EXAMPLE 8

(E,E,E)-3,7-dimethyl-9[(2,4-trimethyl)-3-furyl]-2,4,6,8-nonatetraenoic acid 4-methyl-1-(2-ethylpiperazinyl) ester and (E,E,E)-3,7-dimethyl-9-[](2,4-trimethyl)-3-furyl]-2,4,6,8-nonatetraenoic acid 4-methyl-1-(2-ethylpiperazinyl) ester dihydrochloride In a manner similar to that described in Example 7 (E,E,E)-3,7-dimethyl-9-[(2,4-trimethyl)-3-furyl]-2,4,6,8-nonatetraenoic acid 4-methyl-1-(2-ethylpiperazinyl) ester and its bishydrochloride salt of the formula (E,E,E)-3,7-dimethyl-9-[(2,4-trimethyl)-3-furyl]-2,4,6,8-nonatetraenoic acid 4-methyl-1-(2-ethylpiperazinyl) ester dihydrochloride are prepared from (E,E,E)-3,7-dimethyl-9-(2,4-trimethyl-3-furyl)-2,4,6,8-nonatetraenoic acid.

EXAMPLE 9

(E,E,E)-3,7-dimethyl-9-(2,4,5-trimethyl-3-furyl)-
2,4,6,8-nonatetraenoic acid amide A solution of (E,E,E)-3,7-dimethyl-9-(2,4-dimethyl-3-furyl)-2,4,6,8-nonatetraenoic acid chloride (from 15 g. (E,E,E)-3,7-dimethyl-9-(2,4-dimethyl-3-furyl)-2,4,6,8-nonatetraenoic acid) in ether (150 ml.) is added to a cold mixture (−30°) of ammonia (5 ml.) and ether (25 ml.) and then warmed to room temperature over 2 hours. The mixture is washed with and after removal of the solvents, the residue is crystallized from ethanol to yield (E,E,E)-3,7-diemthyl-9-(2,4,5-trimethyl-3-furyl)-2,4,6,8-nonatetraenoic acid amide.

EXAMPLE 10

(E,E,E)-3,7-dimethyl-9-(2,4-dimethyl-3-furyl)-
2,4,6,8-nonatetraenoic acid amide In a manner similar to that described in Example 9 (E,E,E)-3,7-dimethyl-9-(2,4-dimethyl-3-furyl)-2,4,6,8-nonatetraenoic acid amide is prepared from (E,E,E)-3,7-dimethyl-9-(2,4,5-trimethyl-3-furyl)-2,4,6,8-nonatetraenoic acid chloride.

EXAMPLE 11

Potassium
(E,E,E)-3,7-dimethyl-9-(2,4-dimethyl-3-furyl)-
2,4,6,8-nonatetraenoate and sodium
(E,E,E)-3,7-dimethyl-9-(2,4-dimethyl-3-furyl)-
2,4,6,8-nonatetraenoate (E,E,E)-3,7-dimethyl-9-(2,4,5-trimethyl-3-furyl)-2,4,6,8-nonatetraenoic acid ethyl ester (16 g.) was dissolved in methanol (100 ml.) containing potassium hydroxide (10 g.) and water (20 ml.) and the resulting mixture was heated at reflux for 1 hour. On cooling, a potassium salt crystallized out. This was filtered off, washed with methanol and crystallized from isopropanol-water to give pure potassium (E,E,E)-3,7-dimethyl-9-(2,4-dimethyl-3-furyl)-2,4,6,8-nonatetraenoate, m.p. 265°-70° (dec.).

(E,E,E)-3,7-dimethyl-9-(2,4-dimethyl-3-furyl)-2,4,6,8-nonatetraenoic acid chloride (1.5 g.) was dissolved in a solution of methanol and sodium ethoxide (0.3 g.) and the resulting mixture was then concentrated to dryness to give sodium (E,E,E)-3,7-dimethyl-9-(2,4-dimethyl-3-furyl)-2,4,6,8-nonatetraenoate m.p. ~280° with decomposition as an amorphous solid.

EXAMPLE 12

Potassium
(E,E,E)-3,7-dimethyl-9-(2,4,5-trimethyl-3-furyl)-
2,4,6,8-nonatetraenoate and sodium
(E,E,E)-3,7-dimethyl-9-(2,4,5-trimethyl-3-furyl)-
2,4,6,8-nonatetraenoate In a manner similar to that described in Example 11 potassium (E,E,E)-3,7-dimethyl-9-(2,4,5-trimethyl-3-furyl)-2,4,6,8-nonatetraenoate m.p. 200°-250° decomposition and sodium (E,E,E)-3,7-dimethyl-9-(2,4,5-trimethyl-3-furyl)-2,4,6,8-nonatetraenoate m.p. 210°-260° with decomposition were formed from (E,E,E)-3,7-dimethyl-9-(2,4,5-trimethyl-3-furyl)-2,4,6,8-nonatetraenoic acid ethyl ester.

EXAMPLE 13

(E,E,E)-3,7-dimethyl-9-(2,4-dimethyl-3-furyl)-
2,4,6,8-nonatetraenol (E,E,E)-3,7-dimethyl-9-(2,4-dimethyl-3-furyl)-2,4,6,8-nonatetraenoic acid ethyl ester (6 g.) in ether (25 ml.) was added to a solution of diisobutyl aluminum hydride (38 ml.; 25% by volume in hexane) at −40° and stirred for 30 minutes at room temperature. Aqueous methanol (1:1 parts by volume; 1.6 ml.) was added. The mixture was then carefully warmed to room temperature and then treated with anhydrous magnesium sulfate. The solids were filtered off and the solvents were removed to give (E,E,E)-3,7-dimethyl-9-(2,4,-dimethyl-3-furyl)-2,4,6,8-nonatetraenol as an oil. The pmr spectrum showed the complete absence of ester or aldehyde functions.

EXAMPLE 14

(E,E,E)-3,7-dimethyl-9-(2,4,5-trimethyl-3-furyl)-
2,4,6,8-nonatetraenol

In a manner similar to that described in Example 13, (E,E,E)-3,7-dimethyl-9-(2,4,5-trimethyl-3-furyl)-2,4,6,8-nonatetraenol as a foam, was formed from (E,E,E)-3,7-dimethyl-9-(2,4,5-trimethyl-3-furyl)-2,4,6,8-nonatetraenoic acid ethyl ester.

EXAMPLE 15

(E,E,E)-3,7-dimethyl-9-(2,4,5-trimethyl-3-furyl)-
2,4,6,8-nonatetraenoic acid ethyl ester

| | Tablet Formulation (Direct Compression) | | | | |
|---|---|---|---|---|---|
| | | mg/tablet | | | |
| Item | Ingredients | 0.5 | 5.0 | 10.0 | 25.0 |
| 1 | (E,E,E)-3,7-dimethyl-9-(2,4,5-trimethyl-3-furyl)-2,4,6,8-nonatetraenoic acid ethyl ester | 0.5 | 5.0 | 10.0 | 25.0 |
| 2 | Lactose | 85.5 | 81.0 | 103.0 | 112.5 |
| 3 | Avicel | 30.0 | 30.0 | 45.0 | 60.0 |
| 4 | Modified Starch | 7.5 | 7.5 | 10.0 | 15.0 |
| 5 | Magnesium Stearate | 1.5 | 1.5 | 2.0 | 2.5 |
| | Total | 125 mg. | 125 mg. | 170 mg. | 215 mg. |

Procedure:
1. Mix Items 1–5 in a suitable mixer for 10–15 minutes.
2. Add magnesium stearate (Item 5) as a premix and mix for 4 minutes. Compress on a suitable press.

EXAMPLE 16

(E,E,E,E)-3,7-dimethyl-9-(2,4,5-trimethyl-3-furyl)-2,4,6,8-nonatetraenoic acid ethyl ester

| | | Capsule Formulation | | | |
|---|---|---|---|---|---|
| | | | mg/capsule | | |
| Item | Ingredients | 0.5 | 5.0 | 10.0 | 25.0 |
| 1 | (E,E,E,E)-3,7-dimethyl-9-(2,4,5-trimethyl-3-furyl)-2,4,6,8-nonatetraenoic acid ethyl ester | 0.5 | 5.0 | 10.0 | 25.0 |
| 2 | Lactose | 183.5 | 179.0 | 218.0 | 257.0 |
| 3 | Starch | 30.0 | 30.0 | 50.0 | 70.0 |
| 4 | Talc | 5.0 | 5.0 | 10.0 | 15.0 |
| 5 | Magnesium Stearate | 1.0 | 1.0 | 2.0 | 3.0 |
| | Total | 220 mg. | 220 mg. | 290 mg. | 370 mg. |

Procedure:
1. Mix Items 1–3 in a suitable mixer. Mill through suitable mill.
2. Mix with Items 4 and 5 and fill on capsule machine.

EXAMPLE 17

(E,E,E,E)-3,7-dimethyl-9-(2,4,5-trimethyl-3-furyl)-2,4,6,8-nonatetraenoic acid ethyl ester

| | | Tablet Formulation (Wet Granulation) | | | |
|---|---|---|---|---|---|
| | | | mg/tablet | | |
| Item | Ingredients | 0.5 | 5.0 | 10.0 | 25.0 |
| 1 | (E,E,E,E)-3,7-dimethyl-9-(2,4,5-trimethyl-3-furyl)-2,4,6,8-nonatetraenoic acid ethyl ester | 0.5 | 5.0 | 10.0 | 25.0 |
| 2 | Lactose | 103.5 | 99.0 | 148.0 | 197.0 |
| 3 | Modified Starch | 10.0 | 10.0 | 20.0 | 30.0 |
| 4 | Pregelatinized Starch | 10.0 | 10.0 | 20.0 | 30.0 |
| 5 | Magnesium Stearate | 1.0 | 1.0 | 2.0 | 3.0 |
| | Total | 125 mg. | 125 mg. | 200 mg. | 285 mg. |

Procedure:
1. Mix Items 1–5 in a suitable mixer, granulate with water. Dry, mill.
2. Mix with Item 5 and compress on a suitable press.

EXAMPLE 18

(E,E,E,E)-3,7-dimethyl-9-(2,4-dimethyl-3-furyl)-2,4,6,8-nonatetraenoic acid ethyl ester

| | | Tablet Formulation (Wet Granulation) | | | |
|---|---|---|---|---|---|
| | | | mg/tablet | | |
| Item | Ingredients | 0.5 | 5.0 | 10.0 | 25.0 |
| 1 | (E,E,E,E)-3,7-dimethyl-9-(2,4-dimethyl-3-furyl)-2,4,6,8-nonatetraenoic acid ethyl ester | 0.5 | 5.0 | 10.0 | 25.0 |
| 2 | Lactose | 103.0 | 99.0 | 148.0 | 197.0 |
| 3 | Modified Starch | 10.0 | 10.0 | 20.0 | 30.0 |
| 4 | Pregelatinized Starch | 10.0 | 10.0 | 20.0 | 30.0 |
| 5 | Magnesium Stearate | 1.0 | 1.0 | 2.0 | 3.0 |
| | Total | 125 mg. | 125 mg. | 200 mg. | 285 mg. |

Procedure:
1. Mix Items 1–5 in a suitable mixer, granulate with water. Dry, mill.
2. Mix with Item 5 and compress on a suitable press.

EXAMPLE 19

(E,E,E,E)-3,7-diemthyl-9-(2,4-dimethyl-3-furyl)-2,4,6,8-nonatetraenoic acid ethyl ester

| | | Tablet Formulation (Direct Compression) | | | |
|---|---|---|---|---|---|
| | | | mg/tablet | | |
| Item | Ingredients | 0.5 | 5.0 | 10.0 | 25.0 |
| 1 | (E,E,E,E)-3,7-dimethyl-9-(2,4-dimethyl-3-furyl)-2,4,6,8-nonatetraenoic acid ethyl ester | 0.5 | 5.0 | 10.0 | 25.0 |
| 2 | Lactose | 85.5 | 81.0 | 103.0 | 112.5 |
| 3 | Avicel | 30.0 | 30.0 | 45.0 | 60.0 |
| 4 | Modified Starch | 7.5 | 7.5 | 10.0 | 15.0 |
| 5 | Magnesium Stearate | 1.5 | 1.5 | 2.0 | 2.5 |
| | Total | 125 mg. | 125 mg | 170 mg. | 215 mg. |

Procedure:
1. Mix Items 1–5 in a suitable mixer for 10–15 minutes.
2. Add magnesium stearate (Item 5) as a premix and mix for 4 minutes. Compress on a suitable press.

EXAMPLE 20

(E,E,E,E)-3,7-dimethyl-9-(2,4-dimethyl-3-furyl)-2,4,6,8-nonatetraenoic acid ethyl ester

| Item | Ingredients | Capsule Formation | | | |
|---|---|---|---|---|---|
| | | 0.5 | 5.0 | 10.0 | 25.0 |
| 1 | (E,E,E,E)-3,7-dimethyl-9-(2,4-dimethyl-3-furyl)-2,4,6,8-nonatetraenoic acid ethyl ester | 0.5 | 5.0 | 10.0 | 25.0 |
| 2 | Lactose | 183.5 | 179.0 | 218.0 | 257.0 |
| 3 | Starch | 30.0 | 30.0 | 50.0 | 70.0 |
| 4 | Talc | 5.0 | 5.0 | 10.0 | 15.0 |
| 5 | Magnesium Stearate | 1.0 | 1.0 | 2.0 | 3.0 |
| | Total | 220 mg. | 220 mg. | 290 mg. | 370 mg. |

Procedure:
1. Mix Items 1–3 in a suitable mixer. Mill through suitable mill.
2. Mix with Items 4 and 5 and fill on capsule machine.

I claim:

1. A compound of the formula:

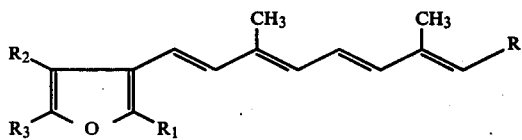

wherein $R_1$ and $R_2$ each are lower alkyl; $R_3$ is hydrogen or lower alkyl; and R is

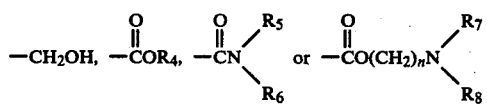

wherein $R_4$ is hydrogen or lower alkyl; $R_5$, $R_6$ $R_7$ and $R_8$ individually are hydrogen or lower alkyl; $R_7$ and $R_8$ can be taken together with the attached nitrogen atom to form a 5 or 6 membered heterocyclic ring which can contain one additional hetero atom selected from the group consisting of nitrogen, oxygen and sulfur, and which hetero atom can be unsubstituted or substituted with lower alkyl; and n is 2 or 3; with the proviso that when $R_7$ and $R_8$ are taken together to form a 5 or 6 membered heterocyclic ring which contains an additional nitrogen atom, said additional nitrogen atom is lower alkyl substituted;
or the pharmaceutically acceptable salts thereof.

2. The compound of claim 1 wherein the compound is all trans.

3. The compound of claim 1 or 2 wherein R is —CH$_2$OH.

4. The compound of claim 1 wherein the compound is (E,E,E,E)-3,7-dimethyl-9-(2,4-dimethyl-3-furyl)-2,4,6,8-nonatetraenol.

5. The compound of claim 1 wherein the compound is (E,E,E,E)-3,7-dimethyl-9-(2,4,5-trimethyl-3-furyl)-2,4,6,8-nonatetraenol.

6. The compound of claim 1 or 2 wherein R is

and $R_4$ is hydrogen or lower alkyl.

7. The compound of claim 6 wherein $R_4$ is hydrogen.

8. The compound of claim 1 wherein the compound is (E,E,E,E)-3,7-dimethyl-9-(2,4,5-trimethyl-3-furyl)-2,4,6,8-nonatetraenoic acid.

9. The compound of claim 1 wherein the compound is potassium (E,E,E,E)-3,7-dimethyl-9-(2,4-dimethyl-3-furyl)-2,4,6,8-nonatetraenoate.

10. The compound of claim 1 wherein the compound is sodium (E,E,E,E)-3,7-dimethyl-9-(2,4-dimethyl-3-furyl)-2,4,6,8-nonatetraenoate.

11. The compound of claim 1 wherein the compounds is (E,E,E,E)-3,7-dimethyl-9-(2,4-dimethyl-3-furyl)-2,4,6,8-nonatetraenoic acid.

12. The compound of claim 1 wherein the compound is potassium (E,E,E,E)-3,7-dimethyl-9-(2,4,5-trimethyl-3-furyl)-2,4,6,8-nonatetraenoate.

13. The compound of claim 1 wherein the compound is sodium (E,E,E,E)-3,7-dimethyl-9-(2,4,5-trimethyl-3-furyl)-2,4,6,8-nonatetraenoate.

14. The compound of claim 6 wherein R is lower alkyl.

15. The compound of claim 1 wherein the compound is (E,E,E,E)-3,7-dimethyl-9-(2,4-dimethyl-3-furyl)-2,4,6,8-nonatetraenoic acid ethyl ester.

16. The compound of claim 1 wherein the compound is (E,E,E,E)-3,7-dimethyl-9-(2,4,5-trimethyl-3-furyl)-2,4,6,8-nonatetraenic acid ethyl ester.

17. The compound of claim 1 or 2 wherein R is

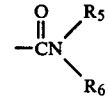

and $R_5$ and $R_6$ individually are hydrogen or lower alkyl.

18. The compound of claim 1 wherein the compound is (E,E,E,E)-3,7-dimethyl-9-(2,4,5-trimethyl-3-furyl)-2,4,6,8-nonatetraenoic acid amide.

19. The compound of claim 17 wherein the compound is (E,E,E,E)-3,7-dimethyl-9-(2,4-dimethyl-3-furyl)-2,4,6,8-nonatetraenoic acid amide.

20. The compound of claim 1 or 2 wherein R is

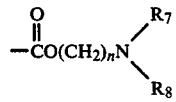

and $R_7$ and $R_8$ individually are hydrogen or lower alky; $R_7$ and $R_8$ can be taken together with the attached nitrogen atom to form a 5 or 6 membered heterocyclic ring which can contain one additional hetero atom selected from the group consisting of nitrogen, oxygen and sulfur and which hetero atom can be unsubstituted or substituted with lower alkyl; and n is 2 or 3; with the proviso that when $R_7$ and $R_8$ are taken together to form a 5 or 6 membered heterocyclic ring which contains an additional nitrogen atom, said additional nitrogen atom is lower alkyl substituted.

21. The compound of claim 1 wherein the compound is (E,E,E,E)-3,7-dimethyl-9-[(2,45-trimethyl)-3-furyl]-2,4,6,8-nonatetraenoic acid 4-methyl-1-(2-ethyl-piperazinyl)ester.

22. The compound of claim 1 wherein the compound is (E,E,E,E)-3,7-dimethyl-9-[(2,4,5-trimethyl)-3-furyl]-2,4,6,8-nonatetraenoic acid 4-methyl-1-(2-ethyl-piperazinyl)ester dihydrochloride.

23. The compound of claim 1 wherein the compound is (E,E,E,E)-3,7-dimethyl-9-[(2,4-trimethyl)-3-furyl]-2,4,6,8-nonatetraenoic acid 4-methyl-1-(2-ethyl-piperazinyl)ester.

24. The compound of claim 1 wherein the compound is (E,E,E,E)-3,7-dimethyl-9-[(2,4-trimethyl)-3-furyl]-2,4,6,8-nonatetraenoic acid 4-methyl-1-(2-ethyl-piperazinyl)ester dihydrochloride.

* * * * *